US006333304B1

(12) United States Patent
Bath et al.

(10) Patent No.: US 6,333,304 B1
(45) Date of Patent: Dec. 25, 2001

(54) THERAPEUTIC COMPOSITIONS CONTAINING GLUCOSAMINE, COLLAGEN AND A BIOFLAVANOL FOR REPAIR AND MAINTENANCE OF CONNECTIVE TISSUE

(76) Inventors: Teresa K. Bath; Neal Lynch, both of 6325 Newland St., Arvada, CO (US) 80003

( * ) Notice: Subject to any disclaimer, the term of this patent is extended or adjusted under 35 U.S.C. 154(b) by 0 days.

(21) Appl. No.: 09/295,001

(22) Filed: Apr. 20, 1999

(51) Int. Cl.$^7$ .......................... A61K 38/00; A61K 38/17; A61K 31/70; A61K 31/715
(52) U.S. Cl. .................... 514/2; 514/8; 514/54; 514/62; 514/801; 530/356
(58) Field of Search .............................. 514/2, 8, 54, 62, 514/801; 530/356

(56) References Cited

U.S. PATENT DOCUMENTS

| | | | |
|---|---|---|---|
| 4,698,360 | * 10/1987 | Masquelier | 514/456 |
| 4,804,745 | 2/1989 | Koepff et al. | 530/356 |
| 4,963,527 | 10/1990 | Bombardelli et al. | 514/25 |
| 5,364,845 | 11/1994 | Henderon | 514/54 |
| 5,650,433 | 7/1997 | Watanabe et al. | 514/456 |
| 5,804,594 | * 9/1998 | Murad | 514/474 |

FOREIGN PATENT DOCUMENTS

WO 98/44929 * 10/1998 (WO) .

OTHER PUBLICATIONS

"Glucosamine and Chondroitin for Treatment of Osteoarthritis—A Systematic Quality Assessment and Meta–analysis", Timothy E. McAlindon, DM, et al., JAMA, Mar. 15, 2000—vol. 283, No. 11, pp. 1469–1475.
"Human Trials," "Veterinary Trials". and "Cell Culture/Animal Models," as summarized by Nutramax Laboratories, Inc., on or before 2001, Edgewood, MD.
"Palaflex™ The Next New Freedom of Movement," VRX® Pharmaceuticals, as summarized by Nutramax Laboratories, Inc., on or before 2001, Edgewood, MD.
"Results of a survey of small–animal practitioners on the perceived clinical efficacy and safety of an oral nutraceutical," M.A. Anderson, et al., Preventive Veterinary Medicine 38 (1999) 65–73.
"Consequin®—Your guide to joint health for dogs," as summarized by Nutramax Laboratories, Inc., on or before 2001, Edgewood, MD.
"Consequin, Nothing else works quite like it!" Nutramax Laboratoaries, Inc., as summarized by Nutramax Laboratories, Inc., on or before 2001, Edgewood, MD.
"Treatment With An Oral Glucosamine–Chondroitin Sulfate Compound for Degenerative Joint Disease in Horses: 25 Cases," Hanson RR, et al., on or before 2001.
"Arthred™ Toxicology and Clinical Studies", *The Traco Functional Foods Series*, Apr. 28, 1993, Traco Labs, Inc., Champaign, IL 61821.

Morreale, P., et al., "Osteoarthritis: Glucosamine Sulfate vs. Chondroitin Sulfate", *Nutrition & Healing*, Jun. 1997, p. 8.
Kim, Jung Ja, et al. "Effect of D–Glucosamine Concentration of the Kinetics of Glucopolysaccharide Biosynthesis in Cultured Thick Embryo Vertebral Cartilage", *Journal of Biological Chemistry*, May 25, 1974, pp. 3091–3097.
Bombardelli, E., et al., "The Flavonoids: New Perspectives in Biological Activities and Therapeutics"; Milano, Italy, on or before Apr. 1999.
Karzel, K., et al., "Effects of Hexosamine Derivatives and Uronic Acid Derivatives on Glycosaminoglycane Metabolism of Fibroblast Cultures", *Pharmacology*, vol. 5, pp. 337–345; University of Bonn; Dec. 23, 1970.
Mulnix, John, et al., "Proanthozone as a Chondroprotective Agent", Animal Health Options, Golden, CO, Jan. 1996.
Kuttan, R., et al., "Collagen treated with (+) catechin becomes resistant to the action of mammalian collagenase", *Experimtia*, vol. 37, pp. 221–223, 1981.
Marx, Jean L., "Oxygen Free Radicals Linked to Many Diseases", *Science*, Jan. 1987, pp. 529–531.
Sokel, R.J., et al., "Antioxidants in Pediatric Gastrointestinal Disease", Pediatric Clinics of North America, vol. 43, No. 2 Apr. 1996, pp. 471–488.
"The Oxygenated Free Radical", European Health News, Ltd., Paris, 1988.
Phelan, Jay, "Time Bomb", Jan. 1991.
Huck, Peter, "The Antioxidant Evolution", HSR Health Supplement Retailer, Jan. 1998, pp 19–26.
Colgan, Michael, *The Flavonoid Revolution*, Apple Publishing, 1997, pp. 5–23.
Dolby, Victoria, "Proanthocyanidins: Powerful Flavonoid Neutralizes Free Radicals", Vitamin Retailer, Nov. 1996, pp. 40–46.
M. Ball, et. al., "Joint Therapy", *Iron Horse*, Nov. 1998, pp. 23–37.
Masquelier, J.,"New Pharmacological Aspects of Certain Flavonoids", English translation from French original. 1969.

(List continued on next page.)

Primary Examiner—Christopher S. F. Low
Assistant Examiner—Abdel A. Mohamed
(74) Attorney, Agent, or Firm—Hogan & Hartson, LLP

(57) ABSTRACT

A composition for treating arthroses in animals includes exogenous glucosamine, hydrolyzed collagen and a bioflavanol. Preferred glucosamines are glucosamine hydrochloride (HCl) and glucosamine sulfate. Preferred bioflavanols are those extracted from grape seeds, pine bark or turmeric root. Proanthocyanidin (also referred to as leucocyanidin or pcynogenol) is the most preferred bioflavanol. With horses and larger animals, a preferred treated method involves application of the composition of the present invention as a top dressing twice a day to the animal's feed. A preferred treatment for humans, dogs and cats involves the ingestion of 1 to 4 tablets or capsules per day of the composition of the present invention.

19 Claims, 2 Drawing Sheets

OTHER PUBLICATIONS

Hansen, Clark, "The Discovery of a Lifetime", © 1994, Arizona Institute of National Medicine.

Uchida, S. et al., "Condensed Tannins Scavenge Active Oxygen Free Radicals", $2^{nd}$ Department of Pharmacology, Nagasaki University School of Medicine, Department of Neurochemistry, Institute of Neurobiology, Okayama University Medical School, Faculty of Pharmaceutical Sciences, Kyushu University, Japan. 1987.

McCord, J.M., "The Superoxide Free Radical: Its Biochemistry and Pathophysiology", Surgery 94:404–406, 1983.

Bucci, L.R., "Chondroprotective Agents: Glucosamine Salts & Chrondroitin Sulfates", Townsend Letter for Doctors, Jan. 1994.

R.W. et al., Eds. *Osteoarthritis, Diagnosis and Medical/Surgical Management*, $2^{nd}$ ed., W.B. Saunders, Philadelphia, 1992, pp. 511–526.

Champe, P.C., Harvey, R.A., *Lippicott's Illustrated Review: Biochemistry*, pp. 32, 81–85, J.B. Lippinott Company, Philadelphia, 1987.

Johnston, S.A., et al., "Osteoarthritis, Joint Anatomy, Physiology Ipathobiology", Osteoarthritis, vol. 27, No. 4, Jul. 1997, pp. 699–723.

Huck, Peter, "Cytotoxic Effect of Grape Seed Extract on Cancer", HSR Health Supplement Retailer. Apr. 1998, p. 41.

Hansen, Clark, "Free Radicals and Antioxidants", © 1997 Vital Formulation, Inc.

Verrengla, Joseph, "These Radicals Terrorize Body", Rocky Mountain News. Jul. 1991.

Levine, S.A. et al., and Kidd, Antioxidant Adaptation: "Its Role in Free Radical Pathology", Biocurrents Division, Allergy Research Group. 1985.

Hitt, M.E., "Oxygen Derived Free Radicals: Pathophysiology and Implications", Compendium Small Animal, vol. 10, No. 8, pp. 939–946. 1988.

Meddleton, E. Jr., "The Flavonoids", Division of Allergy and Clinical Immunology, State University of New York. 1984.

Havsteen, B., "Flavonoids: A Class of Natural Products of High Pharmacological Potency", Department of Biochemistry, School of Medicine. Christian–Albrechts–Universitat Kiel. Kiel, F.R.G., 1983.

Ghosh, P., et al., "Second–Line Agents in Osteoarthritis", Marcel Dekker Inc., New York, 1992, pp. 363–427.

Feine–Haake, G., "A new Therapy for Venous Diseases With 3, 3', 4, 4', 5, 7–," English translation from German original, Zeitschrift for Allemein Mediccal, Stuitgart, Germany, 1975.

"Radical Protection for Athletes," Science News, vol. 141, p. 398, 1992.

Impellizeri, Joseph A., "14 Week Clinical Evaluation of an Oral Antioxidant as a Treatment for Osteoarthritis Secondary to Canine Hip Dysplaysia", Presentation Mar. 5, 1997, $24^{th}$ Annual Meeting of Veterinary Orthopedic Society, Jun. 1997 European College of Veterinary Surgeons, Versailles, France, and Oct., 1997 at Washington State Veterinary Medical Association Meeting.

Pinals, Robert S., "Pharmacologic Treatment of Osteoarthritis", Clinical Therapeutics 14(3):336–346, 1992.

Clark, David M., "The Biochemistry of Degenerative Joint Disease and Its Treatment", *The Compendium*, Small Animal 13(2):275–282, 1991.

Gambhir, Jasvinder K., et al., "Correlation Between Blood Antioxidant Levels and Lipid Peroxidation in Rheumatoid Arthritis", Clinical Biochemistry 30(4):351–355, 1997.

Panasyuk, Andrei, et al., "Effect of Reactive Oxygen Species on the Biosynthesis and Structure of Newly Synthesized Proteoglycans", *Free Radical Biology and Medicine* 16(2):157–167, 1994.

Creamer, Paul, et al., "*Novel Drug Treatment Strategies for Osteoarthritis,*" The Journal of Rheumatology 20(9): 1461–1461, 1993.

Talent, John M., et al., "Pilot Study of Oral Polymeric N–acetyl–D–glucosamine as a Potential Treatment for Patients with Osteoarthritis", Clinical Therapeutics 18(6): 1184–1190, 1996.

Sato, Motoyoshi, et al., "*Antioxidants Inhibit Tumor Necrosis Factor–a Mediated Stimulation of Interleukin–8, Monocyte Chemoattractant Protein–1, and Collagenase Expression in Cultured Human Synovial Cells*", The Journal of Rheumatology 23(3):432–438, 1996.

McCarty, M.F., "Enhanced Synovial Production of Hyaluronic Acid May Explain Rapid Clinical Response to High––dose Glucosamine in Osteoarthritis", Medical Hypotheses 50:507–510, 1998.

11, 1991.

Singh, Raj K., et a "Potential Use of Simple Manganese Salts as ioxidant Drugs in Horses", American Journal of Veterinary Research 53(10): 1822–1829, Oct., 1992.

Lewis, Lon D., Equine Clinical Nutrition, Williams and Wilkins 1995, pp 52–60.

Hawkins, Clare L., et al., "Oxidative Damage to Collagen and Related Substrates by Metal Ion/Hydrogen Peroxide Systems: Random Attack or Site–specific Damage?", Biochimica et Biophysica Acta 1360:84–96, 1997.

Reilly, Patrick M., et al. "Pharmacologic Approach to Tissue Injury Mediated by Free Radicals and Other Reactive Oxygen Metabolites", *The American Journal of Surgery* 161:488–503, Apr. 1991.

Homandberg, G.A., et al, "Fibronectin Fragment Mediated Cartilage Chondrolysis. II. Reparative Effects of Antioxidants", *Biochimica et Biophysica Acta* 1317:143–48, 1996.

Sato, Hideki, et al., "Antioxidant Activity of Synovial Fluid, Hyaluronic Acid, and Two Subcomponents of Hyaluronic Acid", Arthritis and Rheumatism 31(1):63–71, 1988.

Bates, E.J., et al, "Inhibition of Proteoglcan Synthesis by Hydrogen Peroxide in Cultured Bovine Articular Cartilage", *Biochimica et Biophysica Acta* 838:221–28, 1985.

Bates, E.J., et al, "Hyaluronic Acid Synthesis in Articular Cartilage: An Inhibition by Hydrogen Peroxide", Biochimica et Biophysica Res Commun. 132:714–20, 1985.

McIlwraith, C. Wayne, Which is Which? Commentary in Joint Therapy Article, p. 35, The Horse, Nov. 1998.

Tixier, J.M., "Evidence by In Vivo and In Vitro Studies that Binding of Pycnogenols to Elastin Affects its Rate of Degradation by Elastases", Biochemical Pharmacology, 33(24): 3933–39, 1984.

Masquelier, Jacques, "Pycnogenols: Recent Advances in the Therapeutic Activity of Procyanidins", Journal of Natural Products, *Natural Products as Medicinal Agents*: 243–56, 1980.

Houpt, Joseph, and Russell, Allen, presentation of results of Glucosamine HCI clinical trial study. Presented at the 12$^{th}$ Panamerican Congress of Rheumatology in Montreal, Canada, Jun. 22, 1998.

Crolle, G., et al., "Glucosamine suphate for the management of arthrosis: a controlled clinical investigation", *Current Medical Research and Opinion*, 7(2), 1980, pp. 104–109.

Drovanti, A., et al., "Therapeutic Activity of Oral Glucosamine Sulfate in Osteoarthrosis: A Placebo–Controlled Double–Blind Investigation", Clinical Therapeutics, 3(4), 1980, pp 260–272.

* cited by examiner

THERAPEUTIC COMPOSITIONS
CONTAINING GLUCOSAMINE, COLLAGEN
AND A BIOFLAVANOL FOR REPAIR AND
MAINTENANCE OF CONNECTIVE TISSUE

FIELD OF THE INVENTION

The present invention relates to the use of exogenous therapeutic compositions containing glucosamine, hydrolyzed collagen and a bioflavanol for the repair of animal connective tissue, and to therapeutic techniques employing exogenous glucosamine, hydrolyzed collagen and a bioflavanol.

BACKGROUND OF THE INVENTION

Cartilage is the connective tissue which cushions moveable joints. Joint cartilage damage is commonly referred to by a number of terms which are used interchangeably here, including arthritis, arthroses and osteoarthritis. Osteoarthritis is a syndrome characterized by pathologic change of synovial joints accompanied by clinical signs of pain and disability. Unfortunately, most animals have sustained damage to joint cartilage by middle age. Although the causes of degenerative processes are generally unknown, as a general matter, cartilage damage can be classified as one of two forms of osteoarthritis. Primary osteoarthritis occurs when normal forces act on abnormal cartilage causing degeneration. An example is the aging process, where daily physical activity and cellular metabolism create wear and tear on the articular cartilage leading to an arthritic condition. Secondary osteoarthritis occurs when abnormal forces act on normal cartilage causing degeneration. An example is traumatic injury such as tearing the anterior cruciate ligament which may cause enough damage to the joint capsule to lead to arthritis. The result of primary and secondary osteoarthritis is the same—a painful condition in which the animal typically is caught up in a cycle in which the body cannot efficiently repair itself at a rate faster than the rate of degeneration.

Referring now to FIG. 1, it can be seen that a normal joint 10 constitutes the interface between opposing compact bones 1 and 11. Normal joint 10 includes a fibrous joint capsule 3 which defines a joint cavity 5. Joint cavity 5 is lined with a synovial membrane 4 and is filled with synovial fluid 9. Articular cartridge 6 cushions the contact of bones 1 and 11 in normal joint 10.

Referring now to FIG. 2, it can be seen that an arthritic joint 12 exhibits deterioration of articular cartilage 6' as evidenced by worn, irregular and insufficient thicknesses of articular cartilage 6'. The cushioning of the contact between bones 1' and 11' is thereby diminished, which leads to pain and inflammation in the area. The volume of synovial fluid 9' may also be decreased, further diminishing the cushioning ability of arthritic joint 12.

Many factors affect or exacerbate the extent of cartilage deterioration. For example, some animals are predisposed genetically to joint disease and degeneration of joint tissue at an early age. In addition, an animal's genetic makeup can influence the thickness and durability of cartilage which will affect an animal's predisposition to arthritis. Other animals experience abnormal wear and tear on joints as a result of poor conformation and/or excess mechanical stress on musculoskeletal systems. Also, aggressive exercise schedules during youth (as may occur with race horses or athletes) may accelerate the manifestation of joint deterioration problems in later years.

In any case, once the cartilage of a joint is damaged, an inflammatory response ensues. Inflammation itself may be painful, causing the animal to make musculoskeletal adjustments that can exacerbate the joint damage. In addition, inflammation can reduce circulation to the damaged area, preventing needed nutrients and building materials from reaching the damaged area. The body's attempt to repair the damage can even worsen the injury. Degradative enzymes and histamine released at the site of tissue injuries can cause or worsen an arthritic condition. In addition, it is known that as neutrophils invade the area, free radicals (molecules with an electron shortage) are released into the environment causing oxidative damage. Free radicals released in the joint produce further cellular damage before they can be captured by other electrons from surrounding tissues, for example, from cellular membranes, in order to stabilize themselves, which results in a devastating chain reaction causing further tissue damage and inflammation. If cellular membrane damage becomes extensive, cells may die. Free radicals have also been shown to irreversibly break down cartilage matrix proteoglycans.

Initial attempts at dealing with arthroses involved treatment with non-steriodal anti-inflammatory agents such as aspirin. However, as anatomical and physiological knowledge about cartilage, connective tissue and joints has grown, preferred treatments include dietary supplements for use in rebuilding the damaged connective tissue. In the last two decades, popular treatments have focused on one or another substances, reflecting in part, the growing knowledge about cartilage structure and physiology.

It is now known that cartilage fibers and matrix are initially formed by cells called chondroblasts. After cartilage formation is complete, the mature chondrocytes remain in the matrix to produce cartilage as needed to maintain the cartilage. Hyaluronic acid is an acidic mucopolysaccharide present in the extracellular substance of connective tissue which attracts and holds moisture within the connective tissue and complexes to other amino sugars to form the ground substances of the cartilage matrix.

Glucosamine, an amino sugar, is a major constituent of hyaluronic acid and is preferentially taken up by chondrocytes and used in the synthesis of hyaluronic acid. By increasing the amount of hyaluronic acid, glucosamine supplementation leads to the rehydration of cartilage, resulting in increased lubrication and shock absorbing capability. Glucosamine supplementation also leads to an increase in proteoglycans in the extracellular matrix of articular cartilage, thereby increasing the overall amount and the structural integrity of the cartilage.

Glucosamine is also used by chondrocytes to produce glycosaminoglycans, which lead to the production of proteoglycans that hold and hydrate connective tissue. With glucosamine supplementation, chondrocytes may be able to replenish the cartilage matrix and synovial fluid when cartilage is damaged. This is accomplished, in part, because glucosamine increases production of chondroitin sulfate, a glycosaminoglycan which is a component of joint tissue. In addition, chondroitin sulfate inhibits degradative enzymes. However, due in part to the high molecular weight of chondroitin sulfate, chondroitin sulfate is believed to be broken down in the digestive tract for "re-assembly" into chondroitin sulfate in the joint tissue where needed. The breakdown into smaller pieces is significant because one of these smaller pieces is galactosamine which has been shown to decrease or inhibit chondroitin sulfate synthesis, in comparison to a control group in studies.

Studies have been performed to ascertain the effectiveness of glucosamine as a treatment for arthroses in people, dogs and horses. A common view among veterinarians and medical doctors is that the chondroprotective effect of glucosamine is well supported, with results variable but generally positive, and glucosamine considered generally safe for use in joint disease treatment. Surveys of responses indicated that animals and people treated with glucosamine commonly experience some benefit after two or more weeks of treatment. In humans, substantial benefit was experienced after eight or more weeks of treatment. A survey of veterinarians who utilized a glucosamine product to treat dogs with arthritis concluded the product was helpful for improving mobility and alleviating pain. A study of 25 horses diagnosed with degenerative joint disease showed improvement in horses treated with an oral glucosamine formulation.

However, there appears to be substantial variability in positive response of glucosamine treatments compared to placebo treatment. Three glucosamine treatment studies are summarized below in Table I.

TABLE I

| Data Source | Glucosamine Treatment % Positive Response | Time for 50% Response | Placebo Treatment % Positive Response |
| --- | --- | --- | --- |
| Drovanti, et al., "Therapeutic Activity of Oral Glucosamine Sulphate in Osteoarthritis: A Placebo-Controlled Double-Blind Investigation," Clinical Therapeutics, 3(4):266–72, 1980. | 73% | 20 days | 41% |
| Crolle, G., et al., "Glucosamine Sulphate for Management of Arthrosis: A Controlled Clinical Investigation," Current Medical Research and Opinion, 7(2):104–109, 1980. | 27% | 3 weeks | 0% |
| Houpt, J., et al., study presented at July 1998--12th PanAmerican Congress of Rheumatology, Montreal. | 49% | 8 weeks | 45% |

While glucosamine does show a benefit, results are clearly variable, from 27% to 49% to 73% positive results. Discounting by subtraction for placebo effects, positive results range from 4% to 27% to 32%.

One available treatment for the protection and repair of connective tissue is based upon a therapeutic composition comprising glucosamine and salts thereof, chondroitin sulfate, and soluble salts of manganese, and is intended to stimulate production of proteoglycans and collagens in animals. The beneficial effects of the glucosamine in this supplement is a cornerstone of this composition, which appears to be formulated on the premise that the rate-limiting step in the production of collagen is the maturation rather than the production of, newly synthesized collagen. While proponents of this therapy acknowledge that steroids, such as corticosteriods and other anti-inflammatory materials such as high doses of aspirin are widely used for the treatment of arthroses, they caution that such drugs may also inhibit the body's own natural healing processes, leading to further deterioration of the connective tissue.

In other treatment protocols, bioflavanols/flavonoids, terms which are variously identified as including polyphenols, proanthocyanidins, aglycons, glycosides and methylated derivatives, commonly extracted from plants, are being used for their free radical scavenging effect. It has been suggested that the use of plant extracts having proanthocyanidin content are useful for fighting the harmful biological effects of free radicals in collagen degradation, alterations of the synovial liquid, and inflammation. In particular, U.S. Pat. No. 5,650,433 to Watanabe, et al., which issued Jul. 22, 1997 and is entitled Chondroprotective Agents, identifies a chondroprotective agent comprising a flavonoid compound having a specified general formula, as well as glycosides thereof. The patent teaches that this compound strongly inhibits proteoglycan depletion from the chondrocyte matrix, functions to protect cartilage, and is extremely effective for the treatment of arthropathy. However, this patent also teaches that conventional analgesic and anti-inflammatory agents are not effective against the destruction of the articular cartilage, and in fact, sometimes exhibit adverse effect in experiments using chondrocytes.

More particularly, the antioxidant, cardiovascular, circulatory and skin treatment uses of bioflavanols have been studied. One clinical in vivo study of dogs demonstrated the effectiveness of bioflavanols from grape seed extract for treating canine hip dysplasia. The study was randomized and double-blinded. Data was collected from 18 dogs from 1 to 13 years of age having clinical and radiographic evidence of bilateral coxofemoral osteoarthritis secondary to hip dysplasia. All dogs were determined to be free of other musculoskeletal problems based upon history, physical exam, blood count and serum biochemistry profile. Brief lameness exams and dog owners' assessments were conducted at 2, 4, 6, 8, 10, 12 and 14 weeks. Data from this study is summarized in Table II below.

TABLE II

| Data Source | Bioflavanol Treatment % Positive Response | Time for 50% Positive Response | Placebo Treatment % Positive Response |
| --- | --- | --- | --- |
| Impellizeri, J.A., et al., "14-Week Clinical Evaluation of an Oral Antioxidant as a Treatment for Osteoarthritis Secondary to Canine Hip Dysplasia," Syosset Animal Hospital, New York, Veterinary Orthopedic Society 24th Annual Conference, March 1997. | 85.7% | 14 weeks | 9.1% |

Since cartilage regeneration involves the production of collagen built from the amino acids proline, hydroxyproline, hydroxylysine, and glycine, other known therapeutic approaches to treatment of arthroses teach the use of peptides soluble in cold water, in particular, hydrolyzed collagen. In one study, patients with arthroses were administered peptides having an average molecular weight from 40,000 to 60,000 for an extended period, after which they reported, as a whole, a substantial decrease in pain. The patients were scored for the incidence of various arthritis symptoms such as pain, stiffness, weakness, and sensitivity to weather after the substances were administered for 60 days. Additional test data is summarized below in Table III.

TABLE III

| Test Substance | Percentage of Test Participants Exhibiting Specified Reduction in Initial Score after Administration of Test Substances | | |
| --- | --- | --- | --- |
| | <25% | from 25% to 50% | >50% |
| Gelita-Sol D | 19% | 33% | 48% |
| Protein from hen's egg white | 77% | 13% | 10% |
| Gelatin powder | 15% | 29% | 56% |

While the treatments discussed above and other therapies are known for the treatment of arthoses, it can be seen that there remains a need for a therapeutic composition which quickly acts to facilitate the repair of connective tissue while concurrently minimizing ongoing degeneration and providing faster relief from the often high levels of joint pain. It is against that background that the advances of the present invention over individual exogenous glucosamine, hydrolyzed collagen, and bioflavanol therapies for the repair of animal connective tissue have been made.

The present invention relates to a new composition and technique for treating osteoarthritis in animals. The preferred embodiment of a composition of the present invention includes exogenous glucosamine, hydrolyzed collagen and a bioflavanol. Preferred glucosamines are glucosamine hydrochloride (HCl) and/or glucosamine sulfate. Preferred bioflavanols are those extracted from grape seeds, pine bark and turmeric root. Proanthocyanidin (also referred to as leucocyanidin or pcynogenol) is most preferred. With horses and larger animals, a preferred treatment method involves application of the composition of the present invention as a top dressing twice a day to the animal's feed. A preferred treatment for humans, dogs and cats involves the ingestion of 1 to 4 tablets or capsules per day of the composition of the present invention.

DETAILED DESCRIPTION

Figure 1:
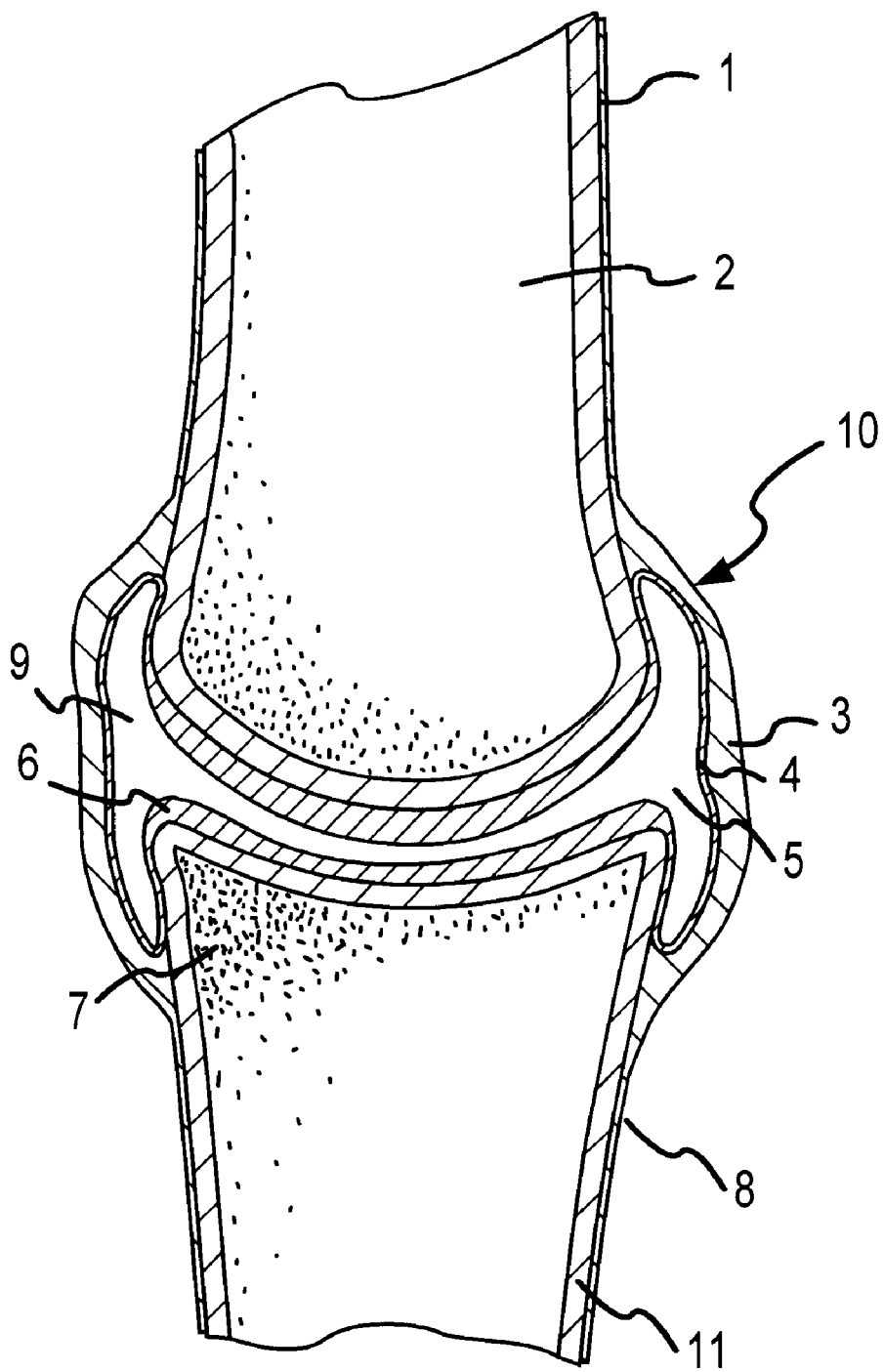
FIG. 1 is an illustrative vertical section of a normal mammalian joint.
Figure 2:
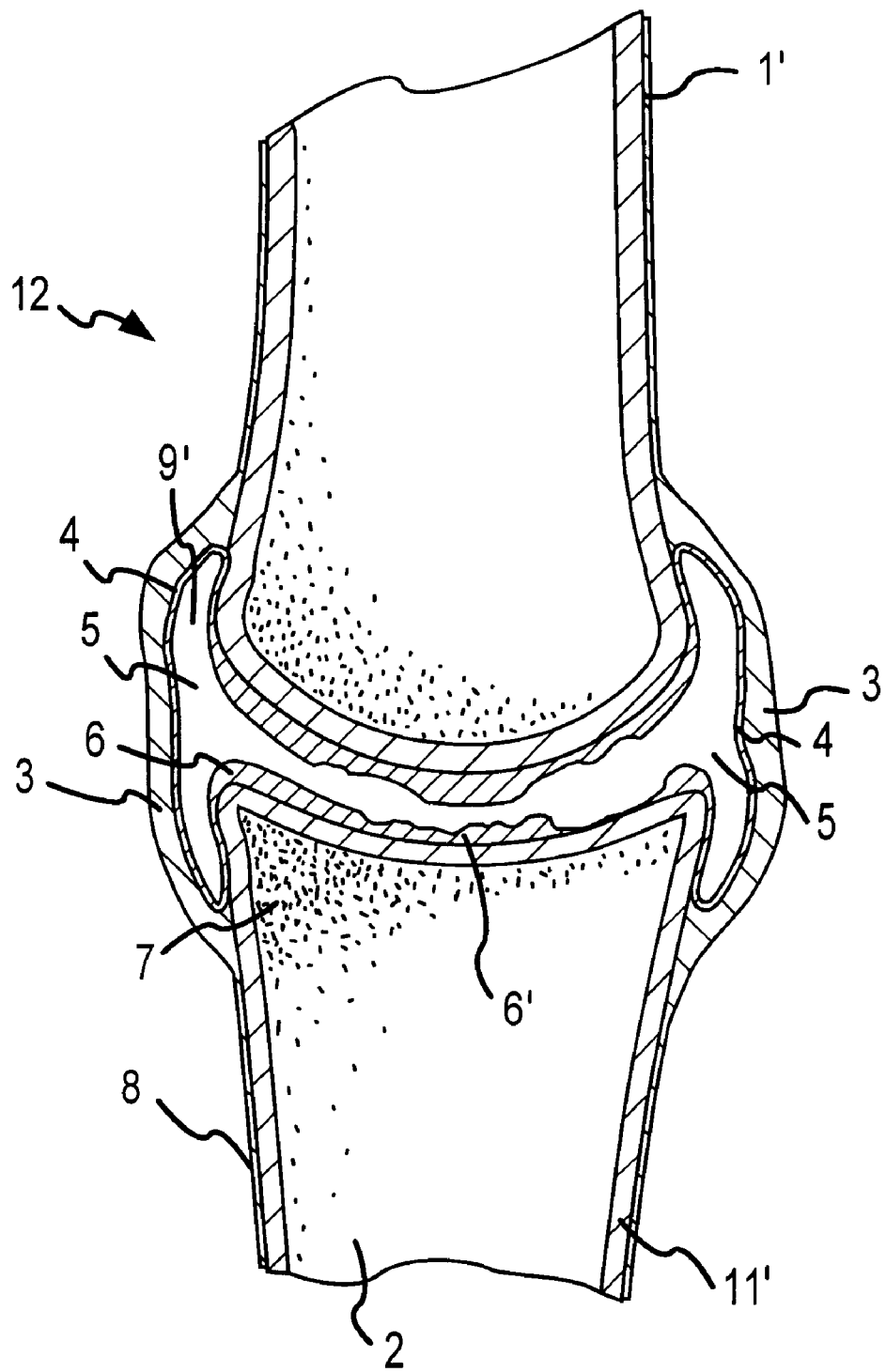
FIG. 2 is an illustrative vertical section of an arthritic mammalian joint.

The present invention relates to a new composition and technique for treating osteoarthritis in animals. The preferred embodiment of the composition of the present invention includes exogenous glucosamine, hydrolyzed collagen and a bioflavanol. Preferred glucosamines are glucosamine hydrochloride (HCl) and/or glucosamine sulfate. Preferred bioflavanols are those extracted from grape seeds, pine bark and turmeric root. Flavan-3-ols, in particular, proanthocyanidin (also referred to as leucocyanidin or Pcynogenol®) are most preferred.

EXAMPLE I

A preferred formulation of a daily recommended dosage of composition of the present invention for use in treating osteoarthritis in horses and other large animals includes three primary ingredients:

| | |
| --- | --- |
| Glucosamine HCl 99+% | 1800 milligrams (mg) |
| Hydrolyzed Collagen | 3500 mg |
| Bioflavanol (grape seed extract) | 300 mg |

The most preferred embodiment also includes three additional ingredients:

| | |
| --- | --- |
| Manganese | 95 mg |
| Zinc | 30 mg |
| Yucca | 500 mg |

This most preferred formulation is preferably provided to the animal in a maintenance dosage of two half measures, applied as a top dress to the animal's feed, with an initial dosage for the first five days of treatment which is twice the maintenance dosage.

EXAMPLE II

A preferred formulation of the present invention for use in treating osteoarthritis in cats, small dogs and other small animals includes:

| | |
| --- | --- |
| Glucosamine HCl 99+% | 420 mg |
| Hydrolyzed Collagen | 240 mg |
| Bioflavanol (grape seed extract) | 10 mg |
| Vitamin C | 15 mg |
| N-acetyl-cysteine | 15 mg |
| Zinc | 2 mg |
| Manganese | 6 mg |

The preferred maintenance dosage for such animals weighing 12 pounds or less is 1 tablet per day containing the above ingredients. The preferred maintenance dosage for such animals weighing from 13 to 25 pounds is 2 tablets per day. An initial dosage for all animals which is twice the maintenance dosage is preferred for the first five days of treatment.

EXAMPLE III

A preferred formulation of the present invention for use in treating osteoarthritis in medium and large dogs and other medium-sized animals includes:

| | |
| --- | --- |
| Glucosamine HCl 99+% | 700 mg |
| Hydrolyzed Collagen | 400 mg |
| Bioflavanol (grape seed extract) | 25 mg |
| Vitamin C | 25 mg |
| N-acetyl-cysteine | 25 mg |
| Zinc | 2 mg |
| Manganese | 10 mg |

The preferred maintenance dosage for such animals weighing from 26 to 50 pounds is 1 tablet per day containing the above ingredients. The preferred maintenance dosage for such animals weighing from 51 to 80 pounds is 2 tablets per day. The,preferred maintenance dosage for such animals weighing over 80 pounds is 3 tablets per day. An initial dosage for all animals which is twice the maintenance dosage is preferred for the first five days of treatment.

EXAMPLE IV

A preferred formulation of the present invention for use in treating osteoarthritis in cats, small dogs and other small animals includes:

| | |
|---|---|
| Glucosamine HCl 99+% | 170 mg |
| Hydrolyzed Collagen | 170 mg |
| Bioflavaonol (grape seed extract) | 2 mg |
| Yucca | 15 mg |
| Vitamin C | 15 mg |
| Vitamin E | 5 IU |
| Zinc | 2 mg |
| Manganese | 1 mg |
| Selenium | 0.02 mg |

The preferred maintenance dosage for such animals weighing 20 pounds or less is 1 tablet per day containing the above ingredients. The preferred maintenance dosage for such animals weighing from 21 to 40 pounds is 2 tablets per day. Initial dose for the first 5 days is double the maintenance dose.

EXAMPLE V

A preferred formulation of the present invention for use in treating osteoarthritis in larger animals includes:

| | |
|---|---|
| Glucosamine HCl 99+% | 250 mg |
| Hydrolyzed Collagen | 250 mg |
| Bioflavanol (grape seed extract) | 3 mg |
| Yucca | 20 mg |
| Vitamin C | 25 mg |
| Vitamin E | 10 IU |
| Zinc | 5 mg |
| Manganese | 2 mg |
| Selenium | 0.02 mg |

The preferred maintenance dosage for such animals weighing 40–60 pounds or less is 1 tablet per day containing the above ingredients.

The preferred dosage for such animals weighing from 61 to 80 pounds is 2 tablets per day. The preferred maintenance dosage for animals weighing over 80 pounds is 3 tablets. Initial dose for the first 5 days is double the maintenance dose.

The preferred formulation includes ingredients previously thought of as therapeutically useful individually or in paired combinations to treat animal arthroses. In particular, glucosamine has been combined with manganese to treat arthroses. However, the inventors of the present invention have determined that the three primary ingredients are all needed for efficient joint repair and maintenance. The lack of any one of the three primary ingredients results in a product that is incomplete when compared to the present treatment technique.

As an initial matter, the inventors of the present invention believe that that while it may be true in generally healthy, young animals that the rate-limiting step in the production of newly synthesized collagen is the maturation rather than the production of the collagen, as has been postulated. In older animals susceptible to arthritic conditions, and in younger animals having an arthrosis resulting primarily from injury, cartilage regeneration may be limited by the availability of these protein constituents which are found in hydrolyzed collagen. By stimulating chondrocytes to greater activity, glucosamine will result in more collagen being produced, but the extent of such increase is dependent upon the availability of the raw materials. Hydroxyproline is an important amino acid component of collagen. Most collagen raw materials, with the exception of hydroxyproline, are readily available from the diet. However, because hydroxyproline is not readily found in food, it must be supplemented to achieve the maximum rate of collagen synthesis. It is postulated that the rate of repair in older or injured animals is more reliant upon the availability of all required nutrients and on the condition of the cartilage in the joint needing rehabilitation, than on the amount of glucosamine present. Thus, hydrolyzed collagen is of particular importance because cartilage is, after all, largely collagen.

It is also important to stop the causes of deterioration to the joint and improve its condition. Quelling inflammation and stopping free radical damage are necessary steps which allow required nutrients to make their way to the chondrocytes and the damaged area, thereby accelerating the cartilage rebuilding process. In particular, flavan-3-ols, and most particularly, proanthocyanidins or leucocyanidins from grape seed extract (or pine bark extract or turmeric root), are preferred for their ability to scavenge free radicals, inhibit mast cell degranulation (cause of inflammatory response), reduce histamine release (cause of inflammatory response), cross link damaged collagen fibers to reduce capillary leakage and inhibit the enzymes that break down collagen and elastin—major structural components of connective tissue.

In any case, the amino sugar, glucosamine, is an essential constituent for the rebuilding of damaged cartilage. Glucosamine supplementation triggers the production of hyaluronic acid (lubricants), chondroitin sulfate (glycosaminoglycans for holding and hydrating connective tissue and enzyme inhibition), keratan, proteoglycans (cartilage shock absorbers) and collagen. While exogenous glucosamine in the form of glucosamine HCl is preferred, glucosamine sulfate and other glucosamine salts are acceptable.

Thus, while the three primary ingredients in the present invention—glucosamine, hydrolyzed collagen, and a bioflavanol—are employed individually or in pairs in other products for the treatment of arthroses, the present invention is the only therapeutic composition for animals known to the inventors hereof, which contains all three primary ingredients. It is believed that all three ingredients are required for an effective joint supplement and repair therapy, with the omission of any one of the three resulting in a product that is incomplete and less efficient.

CASE STUDY I

Three dogs from six to eight years old (two golden retrievers and one Labrador retriever cross) were diagnosed with arthritis and exhibited typical symptoms of lameness, early morning stiffness and paw inflammation. Diagnoses were confirmed with radiography. Each dog was treated with non-steroidal anti-inflammatory drug therapies for two weeks or more, without visible result. Thereafter, a maintenance dosage of two tablets per day of the Example III formulation was administered to each dog. In each case, lameness was visibly diminished in each dog within 7–10 days of treatment, with improvement continuing after 2–3 weeks of treatment. Paw inflammation was eliminated.

CASE STUDY II

A 12 year old chow chow dog, weighing 65 pounds, exhibiting typical symptoms of geriatric arthritis, was administered a maintenance dosage of two tablets per day of the Example III formulation. Lameness was visibly diminished by one week after beginning of treatment. Improvement continued throughout the first month of treatment, with the dog exhibiting substantially increased levels of alertness and activity.

CASE STUDY III

A west highland terrier weighing 20 pounds had been limping for more than two months as a result of hip arthritis. An initial dose of two tablets per day of the Example IV formulation was administered for five days. Thereafter, a maintenance dosage of one tablet per day was administered. Within one month of the start of treatment, no symptoms of the hip problem were visible.

CASE STUDY IV

Five geriatric horses were identified exhibiting arthritic lameness. One daily dose of the Example I formulation was applied as a top dressing to each horse's daily ration. In each case, lameness was noticeably diminished within two weeks after start of treatment. Thereafter, each horse was observed as moving easier and freer and able to withstand a light work schedule.

CASE STUDY V

An eight year old racehorse mare was identified as at risk of injury due to a strenuous workout schedule. The horse was placed on a daily dosage of the Example I formulation applied as a top dressing to the horse's daily ration as a preventive measure and to facilitate healing. The mare withstood the strenuous training schedule, exhibited no signs of injury, and won her next race.

Preferred treatment ranges of the essential three constituents of the formulations of the present invention are summarized in Table IV.

TABLE IV

|  | Glucosamine | Hydrolyzed Collagen | Bioflavanol |
| --- | --- | --- | --- |
| Small animal | 150–350 mg | 150–350 mg | 2–40 mg |
| Human | 250–4200 mg | 500–12000 mg | 30–400 mg |
| Medium and large animals | 250–4200 mg | 250–6000 mg | 25–200 mg |
| Horse and extra large animal | 1000–4200 mg | 2000–12000 mg | 300–1100 mg |

Presently preferred minimum dosages of the therapeutic compositions of the present invention for a horse or other large animal includes a daily dose of the glucosamine hydrochloride of at least 1.5 mg/pound of the animal's weight, a daily dose of proanthocyanidin which is at least 0.2 mg/pound of the animal's weight, and a daily dose of hydrolyzed collagen which is at least 3 mg/pound of the animal's weight. Presently preferred minimum dosages for an adult human includes a daily dose of the glucosamine hydrochloride of at least 1.5 mg/pound of the person's weight, a daily dose of proanthocyanidin which is at least 0.2 mg/pound of the person's weight, and a daily dose of hydrolyzed collagen which is at least 2 mg/pound of the person's weight. Presently preferred minimum dosages for a large dog or other medium sized animal includes a daily dose of the glucosamine hydrochloride of at least 1.5 mg/pound of the animal's weight, a daily dose of proanthocyanidin which is at least 0.2 mg/pound of the animal's weight, and a daily dose of hydrolyzed collagen which is at least 3 mg/pound of the animal's weight. Presently preferred minimum dosages for a cat, small dog or other small animal includes a daily dose of the glucosamine hydrochloride of at least 1.5 mg/pound of the animal's weight, a daily dose of proanthocyanidin which is at least 0.2 mg/pound of the animal's weight, and a daily dose of hydrolyzed collagen which is at least 3 mg/pound of the animal's weight.

In other embodiments of the composition and treatment of the present invention, additional ingredients are included. For example, zinc and manganese are antioxidants which help support the free radical scavenging ability of the bioflavanol. Zinc is also an antioxidant important to healing. It promotes the synthesis of bone tissue, healthy skin and disease resistance. Manganese is an important trace mineral relative to connective tissue. It is needed in enzymes that utilize xylose and galactose in the formation of glycoproteins, which are used to form mucopolysaccharides present in synovial fluid and to form CSA, a sulfated derivative of chondroitin sulfate in the proteoglycan matrix of cartilage. Manganese is normally in low concentrations in connective tissue and supplementation is important to ensure adequate amounts are available for connective tissue synthesis.

Vitamin C may also be added to the compositions of the present invention, as it is important in the building of strong connective tissue. This is because certain structural amino acids need vitamin C in order to be built into cartilage. Collagen tissue built without vitamin C will be weak and ineffective. Since collagen is the key matrix component supporting joint tissue, its strength underlies the strength of the joint overall. Vitamin C is also an important antioxidant and can help reduce the damage done to connective tissue by oxygen free radicals. Vitamin C in the form of a mineral ascorbate is preferred, as glucosaminoglycan synthesis requires several minerals (e.g., zinc, manganese, copper, iron and silicon).

Another embodiment of the present invention includes the addition of N-acetyl-cysteine. N-acetyl-cysteine is an antioxidant that increases the supply of endogenous glutathione in animals, which in turn, decreases collagenase actively. N-acetyl-cysteine donates its sulfur groups to collagen for proper collagen cross-linking and to proteoglycans for proper structural integrity.

Currently, preferred embodiments of the present invention and many improvements have been described with a degree of particularity. It should be understood that the present invention is defined by the spirit and scope of the following claims.

What is claimed is:

1. A therapeutic composition adapted for ingestion, subsequent repair of connective tissue in an aged animal or animal with connective tissue injury and improved movement in the aged or injured animal in less than 4 weeks from initial ingestion of said composition, said composition comprising:
   exogenous hydrolyzed collagen for supplementing the animal's endogenous collagen;
   exogenous glucosamine; and
   an exogenous bioflavanol having anti-inflammatory properties and an ability to cross-link collagen fibers and to inhibit destructive enzymes.

2. A therapeutic composition in accordance with claim 1, wherein the bioflavanol is a polyphenol.

3. A therapeutic composition in accordance with claim 1, wherein the bioflavanol is an extract from the group consisting of grape seed extract, pine bark extract and turmeric root extract.

4. A therapeutic composition in accordance with claim 1, wherein the glucosamine is glucosamine hydrochloride.

5. A therapeutic composition in accordance with claim 1, wherein the glucosamine is glucosamine sulfate.

6. A therapeutic composition in accordance with claim 1, wherein the bioflavanol is proanthocyanidin.

7. A therapeutic composition in accordance with claim 6, wherein the glucosamine is glucosamine hydrochloride.

8. A therapeutic composition in accordance with claim 6, wherein the glucosamine is glucosamine sulfate.

9. A therapeutic technique for treating arthoses in animals by repairing connective tissue injury and maintaining repaired connective tissue in previously injured or aged animals, comprising the step of consistently administering a therapeutically effective amount of a composition comprising exogenous hydrolyzed collagen for supplementing the animal's endogenous collagen, exogenous glucosamine, and a bioflavanol, wherein inflammation in the arthrotic region is reduced to allow connective tissue regeneration and maintenance to proceed and improvement in the arthroses is achieved in less than 4 weeks from initial administration of the composition.

10. The therapeutic technique according to claim 9, wherein the bioflavanol is a polyphenol.

11. The therapeutic technique according to claim 9, wherein the bioflavanol is an extract from the group consisting of grape seed extract, pine bark extract and tumeric root extract.

12. The therapeutic technique according to claim 9, wherein the glucosamine is glucosamine sulfate.

13. The therapeutic technique according to claim 9, wherein the bioflavanol is proanthocyanidin.

14. The therapeutic technique according to claim 13, wherein the glucosamine is glucosamine hydrochloride.

15. The therapeutic technique according to claim 13, wherein the animal undergoing treatment is a horse or other large animal and the total daily dose of the glucosamine hydrochloride is at least 1.5 mg/pound, the total daily dose of the proanthocyanidin is at least 0.2 mg/pound, and the total daily dose of the hydrolyzed collagen is at least 3 mg/pound.

16. The therapeutic technique according to claim 9, wherein the glucosamine is glucosamine hydrochloride.

17. The therapeutic technique according to claim 16, wherein the animal undergoing treatment is an adult human and the total daily dose of the glucosamine hydrochloride is at least 1.5 mg/pound, the total daily dose of the proanthocyanidin is at least 0.2 mg/pound, and the total daily dose of the hydrolyzed collagen is at least 2 mg/pound.

18. The therapeutic technique according to claim 16, wherein the animal undergoing treatment is a large dog or other medium sized animal and the total daily dose of the glucosamine hydrochloride is at least 1.5 mg/pound, the total daily dose of the proanthocyanidin is at least 0.2 mg/pound, and the total daily dose of the hydrolyzed collagen is at least 3 mg/pound.

19. The therapeutic technique according to claim 16, wherein the animal undergoing treatment is a cat, small dog, or other small animal and the total daily dose of the glucosamine hydrochloride is at least 1.5 mg/pound, the total daily dose of the proanthocyanidin is at least 0.2 mg/pound, and the total daily dose of the hydrolyzed collagen is at least 3 mg/pound.

* * * * *